(12) United States Patent
Ishii

(10) Patent No.: US 8,580,849 B2
(45) Date of Patent: Nov. 12, 2013

(54) HYDROUS GEL AND PRODUCTION PROCESS AND USE OF THE HYDROUS GEL

(75) Inventor: Tetsuya Ishii, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 320 days.

(21) Appl. No.: 12/642,560

(22) Filed: Dec. 18, 2009

(65) Prior Publication Data

US 2010/0099636 A1 Apr. 22, 2010

Related U.S. Application Data

(62) Division of application No. 10/516,452, filed as application No. PCT/JP03/07753 on Jun. 18, 2003, now abandoned.

(60) Provisional application No. 60/423,375, filed on Nov. 4, 2002.

(30) Foreign Application Priority Data

Jun. 19, 2002 (JP) .................. 2002-178612

(51) Int. Cl.
*A01N 43/08* (2006.01)
*C08L 53/00* (2006.01)

(52) U.S. Cl.
USPC .............................. 514/474; 525/88; 525/221

(58) Field of Classification Search
None
See application file for complete search history.

(56) References Cited

U.S. PATENT DOCUMENTS

| 6,528,077 | B1 | 3/2003 | Syudo | |
|---|---|---|---|---|
| 2002/0081321 | A1* | 6/2002 | Konno et al. | ................. 424/401 |
| 2003/0012760 | A1 | 1/2003 | Jehn-Rendu et al. | |

FOREIGN PATENT DOCUMENTS

| EP | 1151751 A1 | 11/2001 |
|---|---|---|
| JP | 07-039748 A | 2/1995 |
| JP | 11-047233 A | 2/1999 |
| JP | 2000-143484 A | 5/2000 |
| JP | 2000-212074 A | 8/2000 |
| JP | 2001-064175 A | 3/2001 |
| WO | 01/13915 A1 | 3/2001 |

OTHER PUBLICATIONS

Viscomate Product Information Sheet, May 12, 2008.

* cited by examiner

*Primary Examiner* — Lezah Roberts
*Assistant Examiner* — Nannette Holloman
(74) *Attorney, Agent, or Firm* — Sughrue Mion, PLLC

(57) ABSTRACT

A hydrous gel substantially comprising at least two polymers selected from the group consisting of polyacrylic acid, sodium polyacrylate and partially neutralized polyacrylate, and water, the polymers being crosslinked by containing an aluminum compound, wherein the pH when the hydrous gel is 100-fold diluted with purified water is from 6.5 to 8.5. A hydrous gel which can stably hold an ascorbic acid or a derivative thereof, has high gel strength, exhibits good adhesion to an adherend and causes no liquid syneresis can be provided.

10 Claims, No Drawings

HYDROUS GEL AND PRODUCTION PROCESS AND USE OF THE HYDROUS GEL

CROSS-REFERENCE TO RELATED APPLICATION

The present application is a Divisional of U.S. patent application Ser. No. 10/516,452, filed Dec. 3, 2004, which is a National Stage Entry of PCT/JP03/07753, filed on Jun. 18, 2003, which claims priority from Japanese Patent Application No. 2002-178612 filed Jun. 19, 2002, and from Provisional Application No. 60/423,375 filed Nov. 4, 2002. The entire disclosures of the prior applications are hereby incorporated by reference.

TECHNICAL FIELD

The present invention relates to a hydrous gel containing an ascorbic acid or a derivative thereof, which can stably hold the ascorbic acid or a derivative thereof, can be used for medical preparations for external application (for example, molded poultice, tape agent or plastering agent), cosmetics such as pack, and wound protecting agents, can exhibit high self-shape retentivity and can be easily produced, and also relates to a production process and uses of the hydrous gel.

BACKGROUND ART

An ascorbic acid or a derivative thereof is well known to participate in the biosynthesis of collagen and have a function of keeping, particularly, skin in a firm and fresh state, preventing the production of a melanin pigment giving rise to spots and freckles, and maintaining a beautiful skin. However, when the ascorbic acid or a derivative thereof is formed into a lotion, a cream or the like for the application to skin, such a preparation is not coated in a constant amount to fail in providing a uniform effect or is removed from the skin due to contact with clothing to fail in providing a satisfactory effect.

In order to solve these problems, a method of incorporating an ascorbic acid or a derivative thereof into a hydrous gel having shape retentivity and applying the hydrous gel to skin is known. The hydrous gel used for a plastering agent or a cold insulator is usually constituted by using a natural water-soluble polymer such as tragacanth, acacia, carrageenan, duran gum, sodium alginate, mannan and gelatin, or a synthetic polymer such as polyacrylic acid, polymethacrylate, polyvinyl alcohol and polyacrylamide, as the base and blending therewith a humectant (e.g., polyhydric alcohol), water or the like. However, natural water-soluble polymers in particular are obtained from natural products and, therefore, are not stabilized in quality and, unless these polymers are purified to a higher level, a phenomenon such as contamination by an ingredient mingled or deterioration due to impurities is caused.

For example, Japanese Unexamined Patent Publication No. 2001-64175 (JP-A-2001-64175) discloses a method of preparing a hydrous gel containing an ascorbic acid or a derivative thereof by using two compounds out of magnesium metasilicate aluminate, dried aluminum hydroxide gel and aluminum chloride. This method is, however, insufficient for maintaining the shape retentivity of the gel. The hydrous gel undergoes sagging particularly in the summer season where the hydrous gel is exposed to high temperature, and a so-called strike-through is sometimes caused. Thus, there is still a problem to be solved.

DISCLOSURE OF INVENTION

The present invention has been made under these circumstances and an object of the present invention is to provide a hydrous gel which can stably hold an ascorbic acid or a derivative thereof, has high gel strength, exhibits good adhesion to an adherend, causes no liquid syneresis, has a simple composition to facilitate the preparation, is rapid in the production of gel, and can be produced by an industrial process.

As a result of extensive investigations to solve the above-described problems, the present inventors have found that a hydrous gel substantially comprising at least two polymers selected from the group consisting of polyacrylic acid, sodium polyacrylate and partially neutralized polyacrylate where those polymers are crosslinked by containing a crosslinking agent, particularly an aluminum compound, and the pH when the hydrous gel is 100-fold diluted with purified water is from 6.5 to 8.5, can stably hold an ascorbic acid or a derivative thereof and exhibits excellent gel properties. The present invention has been accomplished based on this finding. The present invention provides the following hydrous gel described in (1) to (13) and a production process and uses of the hydrous gel.

(1) A hydrous gel comprising a gel comprising at least two polymers selected from the group consisting of polyacrylic acid, sodium polyacrylate and partially neutralized polyacrylate crosslinked with an aluminum compound, and water, and an ascorbic acid or a derivative thereof, wherein the pH when the hydrous gel is 100-fold diluted with purified water is from 6.5 to 8.5.

(2) The hydrous gel as described in (1) above, wherein the pH is from 7.0 to 8.0.

(3) The hydrous gel as described in (1) or (2) above, wherein the aluminum compound is magnesium hydroxide-aluminum hydroxide co-precipitate.

(4) The hydrous gel as described in any one of (1) to (3) above, wherein the aluminum compound content is from 0.01 to 10 parts by mass per 100 parts by mass of the hydrous gel.

(5) The hydrous gel as described in any one of (1) to (4) above, wherein the content of the ascorbic acid or the derivative thereof is from 0.01 to 10 parts by mass per 100 parts by mass of the hydrous gel.

(6) The hydrous gel as described in any one of (1) to (5) above, wherein the ascorbic acid derivative is ascorbic acid-2-phosphoric ester or a salt thereof.

(7) The hydrous gel as described in any one of (1) to (6) above, wherein the hydrous gel comprises a polyhydric alcohol.

(8) The hydrous gel as described in any one of (1) to (7) above, wherein when the hydrous gel is formed into a film having a thickness of 0.5 mm and exposed to 25° C. and 60% at relative humidity for 24 hours and then the tackiness on the surface thereof is measured according to the Tack Test Method of JIS 20237, the ball tack value at an inclined angle of 30° is 10 or more.

(9) A process for producing a hydrous gel, comprising preparing a mixture containing at least two polymers selected from the group consisting of polyacrylic acid, sodium polyacrylate and partially neutralized polyacrylate, an aluminum compound, water and an ascorbic acid or a derivative thereof, and heating the mixture at 25 to 65° C.

(10) The process for producing a hydrous gel as described in (9) above, wherein the pH when the hydrous gel is 100-fold diluted with purified water is adjusted to 6.5 to 8.5.

(11) The process for producing a hydrous gel as described in (10) above, wherein the pH is adjusted to 7.0 to 8.0.

(12) A cosmetic material comprising a hydrous gel described in any one of (1) to (8) above.

(13) A preparation for external application comprising a hydrous gel described in any one of (1) to (8) above.

BEST MODE FOR CARRYING OUT THE INVENTION

The present invention is described in detail below.

The hydrous gel of the present invention comprises a gel comprising at least two polymers selected from the group consisting of polyacrylic acid, sodium polyacrylate and partially neutralized polyacrylate crosslinked with an aluminum compound, and water, and an ascorbic acid or a derivative thereof, wherein the pH when the hydrous gel is 100-fold diluted with purified water is from 6.5 to 8.5.

The hydrous gel of the present invention can stably hold an ascorbic acid or a derivative thereof and exhibits excellent gel properties. This hydrous gel has no fluidity, has a strong elastic force and is not easily collapsed even when pressed with a finger. By virtue of these excellent properties, the hydrous gel of the present invention can be applied to various uses, for example, medical products such as plastering agent (e.g., a preparation for percutaneous absorption, a preparation for permucosal absorption), cosmetics and medicated cosmetics such as a pack, a suntan cosmetic and an acne cosmetic.

The content of the ascorbic acid or a derivative thereof for use in the hydrous gel of the present invention is from 0.01 to 10 parts by mass, preferably from 0.5 to 5.0 parts by mass, per 100 parts by mass of the hydrous gel.

The ascorbic acid derivative or a salt thereof is effectively an ascorbic acid derivative or a salt thereof which is enzymatically or non-enzymatically decomposed in vivo and thereby liberates an ascorbic acid. Examples of the ascorbic acid derivative or a salt thereof having such a property include an ascorbic acid-2-phosphoric ester, an ascorbic acid-2-pyrophosphoric ester, an ascorbic acid-2-triphosphoric ester, an ascorbic acid-2-polyphosphoric acid, an ascorbic acid-2,3-diphosphoric ester, an ascorbic acid-2,6-diphosphoric ester, an ascorbic acid-2-sulfuric ester, an ascorbic acid-6-palmitic ester, an ascorbic acid-2,6-palmitic ester, an ascorbic acid-2-glucoside, an ascorbic acid-2-O-glucoside-6-palmitic ester, an ascorbic acid-5,6-benzylidene, an ascorbic acid-5,6-propylidene and their metal salts, ammonium salts and alkyl- or hydroxyalkyl-substituted ammonium salts.

Among these ascorbic acid derivatives, in view of the effect and efficacy, preferred compounds are an ascorbic acid-2-phosphoric ester and salts thereof such as ascorbic acid-2-phosphoric ester magnesium salt and ascorbic acid-2-phosphoric ester sodium salt. The ascorbic acid-2-phosphoric ester is high in the intake rate into a living body as compared with other known ascorbic acid derivatives and also exhibits a high ascorbic acid-liberating rate in vivo. Those salts can be produced by a method described, for example, in Japanese Unexamined Patent Publication No. 44-31237 (JP-A-44-31237), or commercially available products may also be used.

The polyacrylic acid, sodium polyacrylate and partially neutralized polyacrylate, which are a water-soluble polymer used as a base, are low in the irritation to skin and high in the tackiness. Among these polymers, and partially neutralized polyacrylate includes those polymers in which a part of a polyacrylic acid is neutralized with an alkali. Examples of the alkali may include alkali metal salts such as sodium hydroxide and potassium hydroxide, ammonia, aqueous ammonia, primary, secondary and tertiary alkyl amines such as triethanolamine, dimethylamine, diethylamine, trimethylamine, triethylamine, triisopropanolamine and polyethanolamine. The partially neutralized polyacrylate may be prepared by partially neutralizing a polyacrylate or by neutralizing a part of the starting acrylic acid monomer feed and then polymerizing the monomer. The molar ratio of the acrylic acid component to the acrylic acid salt component in the partially neutralized polyacrylate may be preferably 80:20 to 20:80, more preferably 65:35 to 35:65. If the molar ratio exceeds this range, the gelling (ion bonding with aluminum ion, namely, crosslinking reaction) rate is liable to seriously decrease. Typical examples of the partially neutralized polyacrylate may include a sodium acrylate/acrylic acid copolymer, a potassium acrylate/acrylic acid copolymer, an ammonium acrylate/acrylic acid copolymer and the like, but the present invention is not limited to these copolymers. In the hydrous gel of the present invention, the gelling can be made to be proceed easily by using at least two polymers selected from the group consisting of polyacrylic acid, sodium polyacrylate and partially neutralized polyacrylate. The mechanism thereof is not clearly known, but it is considered that, during the proceeding of salt-exchange of sodium salt between a free carboxyl group and a carboxylate in these polymers, ion crosslinking proceeds due to the intervention of an aluminum ion.

For maintaining the shape retentivity of the gel, the content of the aluminum compound added as the crosslinking agent is from 0.01 to 10 parts by mass, preferably from 0.5 to 5.0 parts by mass, per 100 parts by mass of the hydrous gel. If the amount added is less than 0.01 parts by mass, the crosslinking insufficiently proceeds to give poor gel strength and the obtained hydrous gel may be seriously deteriorated in the shape retentivity, whereas if it exceeds 10 parts by mass, the gel is hardened to lack in the flexibility and may be difficult to form into a shape. By changing the amount of the crosslinking agent, the elastic force or flexibility of the gel can be freely controlled and the fitting (adhesion) to skin can be varied.

Examples of the aluminum compound include aluminum chloride, aluminum potassium sulfate, aluminum ammonium sulfate, aluminum nitrate, aluminum sulfate, EDTA-aluminum, aluminum hydroxide-sodium bicarbonate co-precipitate (for example, "Kumulite" produced by Kyowa Chemical Industry Co., Ltd.), synthetic aluminum silicate, aluminum stearate, aluminum allantoinate, synthetic hydrotalcite (for example, "Alcamac", "Alcamizer" and "KYOWORD", produced by Kyowa Chemical Industry Co., Ltd.), magnesium hydroxide-aluminum hydroxide co-precipitate (for example, "Sanalmin" produced by Kyowa Chemical Industry Co., Ltd.), aluminum hydroxide (for example, "Dried Aluminum Hydroxide Gel S-100" produced by Kyowa Chemical Industry Co., Ltd.), aluminum acetate, dihydroxyaluminum aminoacetate (for example, "Glycinal" produced by Kyowa Chemical Industry Co., Ltd.), kaolin, magnesium aluminometasilicate (for example, "Neusilin" produced by Fuji Chemical Industry Co., Ltd.) and magnesium aluminosilicate. The aluminum compound may be either water-soluble or sparingly soluble. Among these, alumina magnesium hydroxide is preferred because the gelling swiftly proceeds and a uniform gel having excellent shape retentivity can be produced. These aluminum compounds can be used individually or in combination of two or more thereof.

In the hydrous gel of the present invention, a crosslinking agent other than the aluminum compound can also be added and examples thereof include inorganic acid salts of calcium, tin, iron, magnesium, manganese, zinc, barium or the like (for example, calcium chloride, magnesium chloride, iron alum, ferric sulfate, magnesium sulfate, EDTA-calcium, EDTA-magnesium, stannous chloride, calcium carbonate, calcium phosphate, calcium hydrogen-phosphate, magnesium carbonate, barium sulfate, magnesium silicate, magnesium stearate and magnesium citrate), hydroxides (for example, calcium hydroxide, barium hydroxide, magnesium hydroxide (e.g., "KISUMA" produced by Kyowa Chemical Industry Co., Ltd.), ferric hydroxide and stannous hydroxide), oxides (for example, magnesium oxide (e.g., "KYOWAMAG", "MAGSALAT", produced by Kyowa Chemical Industry Co., Ltd.)), and epoxy compounds of formaldehyde, ethylene glycol diglycidyl ether, glycerin diglycidyl ether, polyethylene glycol diglycidyl ether, propylene glycol diglycidyl ether and polypropylene glycol diglycidyl ether. These crosslinking agents can be used individually or in combination of two or more thereof.

In the hydrous gel of the present invention, for improving the moisture retentivity of the hydrous gel or enhancing the effect of the ascorbic acid or a derivative thereof, a polyhydric alcohol is preferably added. Examples of the polyhydric alcohol include ethylene glycol, propylene glycol, 1,3-butylene glycol, diethylene glycol, triethylene glycol, 1,4-butylene glycol (dihydric alcohol), glycerin, trioxyisobutane (trihydric alcohol), erythritol, pentaerythritol (tetrahydric alcohol), xylitol, adonitol (pentahydric alcohol), allodulcitol, sorbitol, liquid sorbitol and mannitol (hexahydric alcohol), however, the present invention is not limited thereto.

The pH of the hydrous gel of the present invention is, when the hydrous gel is 100-fold (by mass) diluted with purified water, from 6.5 to 8.5, preferably from 7.0 to 8.0. If the pH exceeds this range, the stability of the ascorbic acid or a derivative thereof is seriously deteriorated and the expected effect cannot obtained. The method for measuring the pH is not particularly limited and a pH meter commonly used may be employed.

The adjustment of the pH is performed for the purpose of not only ensuring stability of the ascorbic acid or a derivative thereof but also controlling the crosslinking rate. Examples of the pH adjusting agent which can be used in the production of the hydrous gel of the present invention include alkalis such as alkali metal hydroxides, alkaline earth metal hydroxides, primary, secondary or tertiary alkylamines, and primary, secondary or tertiary alkanolamines, e.g., sodium hydroxide, potassium hydroxide, calcium hydroxide, magnesium hydroxide, ammonia, aqueous ammonia, triethanolamine, dimethylamine, diethylamine, trimethylamine, triethylamine, triisopropanolamine, tri-sodium phosphate, disodium hydrogenphosphate, dipotassium hydrogenphosphate, monoethanolamine, diethanolamine, diisopropanolamine and polyethanolamine. Furthermore, organic acids, organic acid salts and organic bases having a chelating or coordinating ability for metal ions can be used, such as citric acid, tartaric acid, lactic acid, glycolic acid, hydrochloric acid, nitric acid, malic acid, phosphoric acid, salicylic acid, fumaric acid, methane-sulfonic acid, maleic acid, acetic acid, EDTA-disodium, urea, triethylamine and ammonia. Other than these, inorganic acids such as hydrochloric acid, phosphoric acid, sulfuric acid, nitric acid and hydrobromic acid can be used.

A polymer exhibiting acidity or alkalinity may also be used and examples thereof include an alginic acid, a polyglutamic acid, polyaspartic acid, a starch-acrylic acid graft polymer, a polyacrylate (e.g., potassium poly-acrylate), a carboxyvinyl polymer, a vinyl acetate/crotonic acid copolymer, a vinyl acetate/(meth)acrylic acid copolymer, a vinyl acetate/crotonic acid copolymer, polyvinylsulfonic acid, polyitaconic acid, a styrene/maleic anhydride copolymer and an acrylamide/acrylic acid copolymer, however, the polymer is not limited to these compounds.

In the hydrous gel of the present invention, for improving the moisture retentivity of the hydrous gel or enhancing the effect of the ascorbic acid or a derivative thereof, a solvent and the like may also be added. Examples of the solvent which can be used include water-miscible organic solvents such as alcohols, ketones (e.g., acetone, methyl ethyl ketone), cellosolve, dioxane, dimethylformamide, N-methylpyrrolidone and dimethyl sulfoxide, and water-immiscible organic solvents such as ethyl acetate and crotamiton.

Examples of the alcohols include monohydric alcohols such as methanol, ethanol, propanol, benzyl alcohol, phenethyl alcohol, isopropyl alcohol, isobutyl alcohol, hexyl alcohol, 2-ethylhexanol, cyclohexanol, octyl alcohol, butanol, ethylene glycol monobutyl ether and pentanol; ethylene glycol, propylene glycol, 1,3-butylene glycol, diethylene glycol, triethylene glycol, 1,4-butylene glycol (dihydric alcohol); glycerin, trioxyisobutane (trihydric alcohol); erythritol, pentaerythritol (tetrahydric alcohol); xylitol, adonitol (pentahydric alcohol); allodulcitol, sorbitol, liquid sorbitol and mannitol (hexahydric alcohol), however, the present invention is not limited thereto. Among these, polyhydric alcohols are preferred in view of irritation to skin or moisture retentivity.

In the case of using the hydrous gel of the present invention as a medium for the application of a medicament, the medicament can be mixed with the hydrous gel composition still in a sol state or incorporated into the gel after ripening. A suitable method can be selected according to the properties of the medicament and the initial purpose with respect to the administration site and the release rate.

A large number of medicaments can be administered using the hydrous gel of the present invention and examples thereof include an antiphlogistic anodyne such as salicylic acid, glycol salicylate, methyl salicylate, 1-menthol, camphor, sulindac, sodium trimethine, naproxen, fenbufen, piroxicam, triamcinolone, hydrocortisone acetate, indomethacine, ketoprofen, acetaminophen, mefenamic acid, flufenamic acid, ibufenac, loxoprofen, thiaprofen, pranoprofen, fenpurofen, dichlofenac, sodium dichlofenac, alclofenac, oxyphenbutazone, ibuprofen, felbinac, ketronac, bermoprofen, napmeton, naproxen, flurbipropfen, fluocinonide and clobetasol propionate.

Other examples include corticosteroids, antifungals, antihistamines, hyponic sedatives, ataractics, anti-hypertensives, depressing diuretics, antibiotics, anesthetics, antibacterial substances, vitamin preparations, antiepileptics, coronary vasodilators, antihistamines, antitussives, sexual hormones, antidepressants, angina treating agents, anesthetic anodynes, crude drugs, 5-fluorouracil, dihydroergotamine, fentanil, desmopressin, digoxin, metoclopramide, domperidone, scopolamine, scopolamine hydrobromide, medicaments for animals, sleep-inducing drugs, circulatory system treating agents, cerebral metabolism activating agents, microbicides, enzyme preparations, enzyme inhibitors, biopharmaceuticals (polypeptides), keratosis treating agents, narcotics, antitumor agents, general anesthetics, antianxiety agents, medicines for asthma and nasal allergy, antiparkinsonism agents, chemical treating agents, vermicide, antiprotozoiasis agents, arthrifuges, styptics, cardiac agents, stimulant•antihypnotics, medicines for habitual toxipathy, Chinese herbal medicines, radiopharmaceutical agents, medicines for urogenital system and anus, blood sugar decreasing agents, antiulcer agents, medicines for head hair, sequestering agents, rubefacients, antisweating agents, tranquilizers, blood anticoagulants, antirheumatics, antigout agents and coagulant agents, however, the present invention is not limited thereto. These medicaments can be used in combination of two or more, if desired.

An auxiliary agent of accelerating the absorption of the ascorbic acid or a derivative thereof may also be added and examples thereof include a keratin softening agent such as ethyl alcohol, isopropyl alcohol, butanol, 1,3-butanediol, propylene glycol, polyethylene glycol #400, glycerin, crotamiton, benzyl alcohol, phenyl ethyl alcohol, propylene carbonate, hexyl dodecanol, propanol, allantoin, dimethylsulfoxide, dimethylacetamide, dimethylformamide, diisopropyl adipate, diethyl sebacate, ethyl laurate, lanolin, azone, 1-geranylazacycloheptan-2-one (GACH), fatty acid dialkylolamide, salicylic acid, salicylic acid derivative, urea and sulfur; a humectant such as pyrrolidone carboxylic acid; a surfactant such as propylene glycol monooleate, polyoxyethylene sorbitan monostearate, sorbitan monostearate and glycerin monostearate; an ester such as isopropyl myristate and diethyl sebacate; a higher alcohol such as oleyl alcohol, stearyl alcohol and lauryl alcohol; a fatty acid such as stearic acid, hexanoic acid, nonanoic acid, decanoic acid, dodecanoic acid, tetradecanoic acid, hexadecanoic acid, octadecanoic acid, oleic acid and linoleic acid; a terpene-base compound such as menthol, menthone, limonene, pinene, piperitone, terpinene, terpinolene, terpinol and carveol; and an oil ingredient such as almond oil, olive oil, camellia oil, persic oil, peppermint oil, sesame oil, soybean oil, mink oil, cottonseed oil, corn oil, safflower oil, coconut oil, eucalyptus oil, castor oil, liquid paraffin, vaseline, squalene, squalane and lanolin. One or more of these ingredients can be blended. In view of skin irritation or the like, such an auxiliary agent is preferably blended in an amount of 0.1 to 5 parts by mass per 100 parts by mass of the hydrous gel.

In the hydrous gel of the present invention, other active ingredients may be used in combination and those commonly known as an active ingredient can be freely added, such as antiacne agents, antiandrogens, bactericides, antiinflammatory agents, antioxidants, radical scavengers and whitening agents. Examples of the antiandrogen active ingredient used in combination include cyproterone acetate, spironolactone, estrogen and glucocorticoid; examples of the bactericide active ingredient used in combination include an antibiotic such as erythromycin, clindamycin, gentamycin, penicillin, chloramphenicol and tetracycline, and an antibacterial ingredient such as benzoyl peroxide, nadifloxacin, ethanol, benzalkonium chloride, sulfur, parahydroxybenzoate esters, salicylic acid, hinokitiol, triclosan and homosulfamine; and examples of the antiinflammatory used in combination include ibuprofen piconol, glycyrrhitin, camphor and indomethacin.

Examples of the antiacne active ingredient used in combination include tretinoin, resorcin, isopropyl methyl phenol, tocopherol and ascorbic acid. Examples of the whitening active ingredient used in combination include placenta extract, kojic acid, ellagic acid, arbutin and tranexamic acid ester. Other than these, plant-originated antibacterial, antibacterial and antiinflammatory ingredients can be used in combination, such as chamomile extract, sasa albo-marginata extract, rose extract, balm mint extract, gentian extract, glycyrrhiza extract, jojoba extract, rosemary extract, sage extract, thyme extract, lavender extract, paeonia extract, ginseng extract, aloe extract, soy extract, perilla extract, mugwort extract, tumeric extract, hinoki leaf extract, hinoki extract, Rhei Rhizoma extract, phellodendron bark extract, Japanese coptis extract, ginkgo extract, mulberry bark extract, green tea extract, grapefruit bark extract, araliaceous extract, gynostemma pentaphyllum extract and various seaweed extracts. Such an active ingredient used in combination is added in an amount of 0.01 to 50 mass % based on the hydrous gel, though this varies depending on the kind and use of the ingredient.

In the hydrous gel of the present invention, for the purpose of more successfully bringing out the characteristics of the hydrous gel, improving the processing and shaping property and the quality, or improving the dispersibility and stability of the ascorbic acid or a derivative thereof in the gel, a compound selected according to the purpose can be further arbitrarily blended to an extent of not impairing the performance of the hydrous gel.

These additives include:

(1) Moisturizer:

for example, glycerin, propylene glycol, sorbitol, 1,3-butylene glycol, dl-pyrrolidonecarboxylic acid and sodium lactate;

(2) Astringent:

for example, citric acid, tartaric acid, lactic acid, aluminum chloride, aluminum sulfate, allantoin chloro-hydroxyaluminum, allantoin dihydroxyaluminum, aluminum phenolsulfate, zinc paraphenolsulfonate, zinc sulfate and aluminum chlorohydroxide;

(3) Humectant:

for example, polyhydric alcohols such as glycerin, propylene glycol, 1,3-butylene glycol, sorbitol, polyglycerin, polyethylene glycol and dipropylene glycol; NMF ingredients such as sodium lactate; and water-soluble polymers such as hyaluronic acid, collagen, mucopoly-saccharide and chondroitin sulfate;

(4) Thickener:

for example, natural polymers such as gum arabic, tragacanth gum, locust bean gum, guar gum, echo gum, karaya gum, agar, starch, carrageenan, alginic acid, alginates (e.g., sodium alginate), propylene glycol alginate, dextran, dextrin, amylose, gelatin, collagen, pullulan, pectin, amylopectin, starch, sodium amylopectin semiglycolate, chitin, albumin and casein; semi-synthetic polymers such as polyglutamic acid, polyaspartic acid, methylcellulose, ethylcellulose, propylcellulose, ethylmethylcellulose, hydroxyethylcellulose, hydroxypropylcellulose, hydroxy-propylmethylcellulose, carboxymethyl starch, alkali metal carboxymethylcellulose, alkali metal cellulose sulfate, cellulose graft polymer, crosslinked gelatin, cellulose acetate phthalate, starch-acrylic acid graft copolymer, phthalic anhydride-modified gelatin and succinic acid-modified gelatin; and synthetic polymers such as polyvinyl alcohol, polyvinylpyrrolidone, polyvinyl methyl ether, carboxyvinyl polymer, vinylpyrrolidone/ethyl acrylate copolymer, vinylpyrrolidone/styrene copolymer, vinylpyrrolidone-vinyl acetate copolymer, vinyl acetate/(meth)acrylic acid copolymer, vinyl acetate/crotonic acid copolymer, N-vinylacetamide base copolymers (e.g., N-vinylacetamide/sodium acrylate copolymer), crosslinked N-vinylacetamide polymer, polyitaconic acid, polyhydroxyethyl acrylate, polyacrylamide, styrene/maleic anhydride copolymer and acrylamide/acrylic acid copolymer;

(5) Tackifying Substance:

for example, tackifying substances such as silicone rubber, polyisoprene rubber, styrene block copolymer rubber, acrylic rubber and raw rubber;

(6) Anti-Itching Agent:

for example, camphor, thymol, menthol, polyoxy-ethylene lauryl ether, antihistamine and ethyl aminobenzoate;

(7) Keratin Softening and Abrading Agent:

for example, sulfur, thioxolone, selenium sulfide, salicylic acid and resorcin;

(8) Accidental Ingestion Preventing Substance:

for example, red pepper powder and red pepper essence;

(9) Powder Raw Material:

for example, montmorillonite, silicic anhydride, gypsum, carbon black, diatomaceous earth, red oxide of iron, calcium carbonate, hydrotalcite, talc, glass, kaolin, bentonite, metal soap, aerosil, titanated mica, bismuth oxychloride, fish scale flake, zinc white and titanium dioxide;

(10) Oily Raw Material:

for example, almond oil, olive oil, hardened oil, camellia oil, castor oil, Japan wax oil, coconut oil, beeswax, spermaceti, lanolin, carnauba wax, candelilla wax, liquid paraffin, vaseline, microcrystalline wax, ceresin, squalene, lauric acid, myristic acid, palmitic acid, stearic acid, isostearic acid, oleic acid, lauryl alcohol, cetanol, stearyl alcohol, oleyl alcohol, octyldodecanol, cholesterol, hexyldecanol, white sterol, cetyl lactate, isopropyl myristate, hexyl laurate, myristyl myristate, isopropyl palmitate, octyldodecanol myristate, butyl stearate, cacao oil, Japan wax, jojoba oil, grape seed oil, avocado oil, mink oil, egg yolk oil, beeswax, spermaceti, lanolin, carnauba wax, candelilla wax, liquid paraffin, ceresin wax, paraffin wax, behenic acid, isopropyl adipate, octyldodecyl myristate, octyldodecyl oleate and cholesterol oleate;

(11) Surfactant:

for example, anionic surfactants such as lauryl sulfate, polyoxyethylene alkyl ether sulfate, alkylbenzene-sulfonate, polyoxyethylene alkyl ether phosphoric acid, polyoxyethylene alkyl phenyl ether phosphoric acid, N-acylamino acid salt, sodium stearate, potassium palmitate, sodium cetylsulfate, sodium laurylsulfate, triethanolamine palmitate, sodium polyoxyethylenelaurylphosphate, sodium acylglutamate and surfactin; cationic surfactants such as benzalkonium chloride, benzetonium chloride, stearyl-trimethylammonium chloride, distearyldimethylammonium chloride and stearyldimethylbenzylammonium chloride; amphoteric surfactants such as alkyldiaminoethylglycine hydrochloride, 2-alkyl-N-carboxymethyl-N-hydroxyethyl-imidazolinium betaine, lauryl dimethylaminoacetic acid betaine and lecithin; and nonionic surfactants such as polyol fatty acid ester, glycerol monostearate, lipophilic glycerol monooleate, ethylene glycol monostearate, propylene glycol monostearate, sorbitan fatty acid ester, polyoxyethylene sorbitan fatty acid ester, polyoxyethylene fatty acid ester, polyoxyethylene alkyl ether, polyoxyethylene alkyl phenol ether, polyoxyethylene sorbitol fatty acid ester, N-acylamino acid ester, sucrose fatty acid ester, fatty acid alkylolamide, polyoxyethylenated sterol, polyoxyethylenated lanolin and polyoxyethylene hydrogenated castor oil;

(12) Coloring Agent:

for example, yellow iron oxide, red iron oxide, black iron oxide, ultramarine, carbon black, chromium hydroxide, chromium oxide, tar pigment, lake, Food Red 2, Food Red 3, Food Red 102, Food Red 201, Food Yellow 4, Food Yellow 5, Food Blue 1 and Food Blue 2;

(13) Perfume:

for example, plant perfumes such as mustard oil, orange oil, sesame oil, jasmine oil, Japan cedar oil, iris oil, terpine oil, orange flower oil, rose oil, eucalyptus oil, lime oil, lemon oil, Japanese mint oil and rosemary oil; animal perfumes such as musk, civet, castoreum and ambergris; hydrocarbon-base perfumes such as bromostyrol, pinene and limonene; alcohol-base perfumes such as benzyl alcohol and 1-menthol; ester-base perfumes such as ethyl acetate and methyl salicylate; aldehyde-base perfumes such as benzaldehyde and salicylaldehyde; ketone-base perfumes such as camphor, muscone, musk ketone and 1-menthone; ether-base perfumes such as safrol; phenol-base perfumes such as thymol; lactone-base perfumes; acid-base perfumes such as phenylacetic acid; and nitrogen compound-base perfumes such as indole;

(14) Ultraviolet Light Shielding Agent:

for example, a benzophenone type such as ASL-24, Cyasorb UV-9 and Uvinul M-40; a benzoic acid type such as Salol; an azole type such as Tinuvin P; a nitrile type such as Uvinul N-35; a urea type such as Ancour UA; a p-amino acid type such as Neo Heliopan Give tan F, 2-hydroxy-4-methoxybenzophenone, octyldimethyl p-aminobenzoate and ethylhexyl p-methoxycinnamate; a salicylic acid type; a benzofuran type; a coumarin type; and an azole type;

(15) Antiseptic and Microbicide:

for example, acids such as benzoic acid, salicylic acid, dehydroacetic acid, sorbic acid and boric acid; salts of these acids; phenols such as phenol, chlorocresol, chloroxylenol, isopropylmethylphenol, resorcin, o-phenyl-phenol, p-oxybenzoic acid ester, phenoxyethanol, thymol, hinokitiol and thioxolone; halogenated bisphenols such as hexachlorophene and 2,4,4'-trichloro-2'-hydroxydiphenyl ether; amide compounds such as trichlorocarbanilide, halocarban and undecylenic acid monoethanolamide; quaternary ammonium compounds such as benzalkonium chloride, alkylisoquinolinium bromide, benzethonium chloride and cetylpyridinium chloride; amphoteric surfactants such as lauryl di(aminoethyl)glycine; 2-pyridinethiol-1-oxide zinc salt; gluconic acid; chlorhexidine; thiram; N-trichloromethylthio-4-cyclohexene-1,2-dicarboximide; and chlorobutanol;

(16) Antioxidant:

for example, nordihydroguaiaretic acid, guaiacum, propyl gallate, butyl hydroxyanisole, dibutylhydroxytoluene (BHT), tocopherol (vitamin E) and 2,2'-methylenebis(4-methyl-6-tert-butyl)phenol;

(17) Chelating Agent:

for example, edetate, pyrophosphate, hexameta-phosphate, citric acid, tartaric acid and gluconic acid;

(18) Ultraviolet Scattering Agent:

for example, titanium oxide, kaolin and talc; and

(19) Solvent:

for example, water-miscible organic solvents such as ketones (e.g., acetone, methyl ethyl ketone), cellosolve, dioxane, dimethylformamide, N-methylpyrrolidone and dimethylsulfoxide; water-immiscible organic solvents such as crotamiton; and alcohols such as methanol, ethanol, propanol, benzyl alcohol, phenethyl alcohol, isopropyl alcohol, isobutyl alcohol, hexyl alcohol, 2-ethylhexanol, cyclohexanol, octyl alcohol, butanol and pentanol.

In addition, a stabilizer, a filler, a preservative, a plasticizer, a softening agent, a deterioration inhibitor and the like may be used and these additives can be freely added within the range of not adversely affecting the properties of the hydrous gel obtained.

When the hydrous gel of the present invention is formed into a film having a thickness of 0.5 mm and exposed to 25° C. and 60% at relative humidity for 24 hours and then the tackiness on the surface thereof is measured according to the Tack Test Method of JIS 20237, the ball tack value at an inclined angle of 30° is 10 or more.

The process for producing the hydrous gel of the present invention is described below.

The process for producing a hydrous gel of the present invention comprising preparing a mixture containing at least two polymers selected from the group consisting of polyacrylic acid, sodium polyacrylate and partially neutralized polyacrylate, an aluminum compound, water and an ascorbic acid or a derivative thereof, and heating the mixture at 25 to 65° C.

The heating temperature is preferably from 35 to 55° C., more preferably from 40 to 50° C. If the heating temperature is less than 25° C., the gelling takes a long time, whereas if it exceeds 65° C., the stability of the ascorbic acid or a derivative may not be obtained.

The gel of the present invention may be manufactured, for example, by a process where an ascorbic acid or a derivative thereof, an aluminum compound, water, a polyacrylic acid and the like are dispersed in a polyhydric alcohol, the dispersion solution is kneaded while adding it to water containing a pH adjusting agent, other additives are added, if desired, and then the kneaded material is heated.

In the production process of the present invention, the hydrous gel is shaped in the sol state after mixing of a crosslinking agent and heated, if desired, thereby performing after-crosslinking. Or, the hydrous gel after crosslinking is directly formed into various shaped articles using an appropriate forming machine, tablet machine or the like. Incidentally, when heated, the gelling speed can be increased.

The sheet of the hydrous gel may be attained by coating an appropriate amount of the hydrous gel on one surface or both surfaces of a support, for example, paper, wood, metal, glass fiber, cloth (e.g., flannel, woven fabric, nonwoven fabric), synthetic resin (e.g., polyurethane, ethylene/vinyl acetate copolymer, polyvinyl chloride, polyester (e.g., polyethylene terephthalate), polyolefin (e.g., polyethylene, polypropylene), polyamide (e.g., nylon 6, nylon 66), polyvinylidene chloride, polytetrafluoroethylene), metal foil (e.g., aluminum), rubber, cellulose derivative, a molded article such as laminate film thereof with plastic film, a sheet (foil) or a tape. For facilitating the storage of the obtained sheet-like hydrous gel, it is preferred that a release sheet treated with silicone or by other appropriate method is affixed to the surface coated with the hydrous gel, or the surface which is not coated with a pressure-sensitive adhesive is treated with silicone or by other appropriate method to form a release surface, and this is rolled over or superposed on the surface where the gel is not coated. Examples of the release sheet which can be used include polyethylene film, polypropylene film, release paper, cellophane, polyvinyl chloride and polyester.

The present invention is further illustrated below by referring to Examples and Comparative Examples, however, the present invention is not limited to these examples. In the examples, the "parts" is "parts by mass".

EXAMPLE 1

A hydrous gel was prepared according to the following raw material blending ratio and formulation.

| Raw Material Blending Ratio | |
| --- | --- |
| Sodium polyacrylate | 2 parts |
| Acrylic acid/sodium acrylate (50/50 (by mol)) copolymer | 2 parts |
| Glycerin | 30 parts |
| magnesium hydroxide-aluminum hydroxide co-precipitate | 1 part |
| Water | 61 parts |
| Diisopropanolamine | 1 part |
| Magnesium ascorbic acid-2-phosphate | 3 parts |

Formulation

A glycerin dispersion solution of magnesium ascorbic acid-2-phosphate ("Ascorbic Acid PM" produced by Showa Denko K.K.), sodium polyacrylate ("Viscomate F480SS" produced by Showa Denko K.K.), acrylic acid/sodium acrylate (50/50 (by mol)) copolymer (partially neutralized polyacrylate) ("Viscomate NP-700" produced by Showa Denko K.K.) and a magnesium hydroxide-aluminum hydroxide co-precipitate ("Sanalmin" produced by Kyowa Chemical Industry Co., Ltd.) was kneaded while gradually adding these to an aqueous solution of diisopropanolamine. The obtained sol was coated on a polypropylene-made liner by a knife coater with a clearance of 0.5 mm, a nonwoven fabric was then affixed on the sol, the whole was placed in an aluminum laminate bag, and the bag was heat-sealed. After ripening for 3 days, a plastering agent was obtained. When the gel on the nonwoven fabric was touched with a finger, the gel was slightly extended and exhibited strong resiliency. The gel was 100-fold diluted with purified water and measured on the pH, as a result, the pH was 8.2. Also, the obtained plastering agent was exposed to 25° C. and 60% at relative humidity for 24 hours and thereafter measured on the ball tack value at an inclined angle of 30° according to the Tack Test Method of JIS 20237, as a result, the ball tack value was 14.

EXAMPLE 2

A hydrous gel was prepared according to the following raw material blending ratio and formulation.

| Raw Material Blending Ratio | |
| --- | --- |
| Sodium polyacrylate | 2 parts |
| Acrylic acid/sodium acrylate (70/30 (by mol)) copolymer | 2 parts |
| D-Sorbitol solution | 30 parts |
| Purified water | 61.5 parts |
| Aluminum hydroxide | 0.5 parts |
| Dihydroxyaluminum aminoacetate | 0.5 parts |
| Diisopropanolamine | 0.5 parts |
| Zinc ascorbic acid-2-phosphate | 3 parts |

Formulation

A D-sorbitol (70 w/v % aqueous solution of D-sorbitol) dispersion solution of zinc ascorbic acid-2-phosphate, sodium polyacrylate, acrylic acid/sodium acrylate (70/30 (by mol)) copolymer (partially neutralized polyacrylate) and dihydroxyaluminum aminoacetate ("GLYCINAL" produced by Kyowa Chemical Industry Co., Ltd.) and aluminum hydroxide ("Dried Aluminum Hydroxide Gel S-100" produced by Kyowa Chemical Industry Co., Ltd.) was kneaded while adding these all at once to an aqueous solution of diisopropanolamine. The obtained sol was coated on a polypropylene-made release paper by a knife coater with a clearance of 0.5 mm, a nonwoven fabric was then affixed on the sol, the whole was placed in an aluminum laminate bag, and the bag was heat-sealed. After ripening for 3 days, a plastering agent was obtained. When the gel on the nonwoven fabric was touched with a finger, the gel was slightly extended and exhibited strong resiliency. The pH of the gel was measured in the same manner as in Example 1 and found to be 8.5. Also, the obtained plastering agent was exposed to 25° C. and 60% at relative humidity for 24 hours and thereafter measured on the ball tack value at an inclined angle of 30° according to the Tack Test Method of JIS 20237, as a result, the ball tack value was 22.

EXAMPLE 3

A hydrous gel was prepared according to the following raw material blending ratio and formulation.

| Raw Material Blending Ratio | |
| --- | --- |
| Sodium polyacrylate | 2 parts |
| Acrylic acid/sodium acrylate (80/20 (by mol)) copolymer | 2 parts |

-continued

| Raw Material Blending Ratio | |
|---|---|
| magnesium hydroxide-aluminum hydroxide co-precipitate | 0.5 parts |
| Aluminum hydroxide | 0.5 parts |
| Propylene glycol | 30 parts |
| Purified water | 61 parts |
| Sodium ascorbic acid-2-phosphate | 4 parts |

Formulation

A glycerin dispersion solution of sodium ascorbic acid-2-phosphate ("Ascorbic Acid PS" produced by Showa Denko K.K.), sodium polyacrylate ("Viscomate F480SS" produced by Showa Denko K.K.), acrylic acid/sodium acrylate (80/20 (by mol)) copolymer (partially neutralized polyacrylate) and magnesium hydroxide-aluminum hydroxide co-precipitate ("Sanalmin" produced by Kyowa Chemical Industry Co., Ltd.) and aluminum hydroxide ("Dried Aluminum Hydroxide Gel S-100" produced by Kyowa Chemical Industry Co., Ltd.) was kneaded while gradually adding these to water. The obtained sol was shaped with a clearance of 0.5 mm, sealed, ripened at 50° C. for 1 day and then taken out from the container to obtain a gel-like pack agent. When the gel was touched with a finger, the gel was extended and exhibited strong resiliency. The pH of the gel was measured in the same manner as in Example 1 and found to be 7.4. Also, the obtained pack agent was exposed to 25° C. and 60% at relative humidity for 24 hours and thereafter measured on the ball tack value at an inclined angle of 30° according to the Tack Test Method of JIS 20237, as a result, the ball tack value was 18.

EXAMPLE 4

A hydrous gel was prepared according to the following raw material blending ratio and formulation.

| Raw Material Blending Ratio | |
|---|---|
| Sodium acrylate/acrylic acid (80/20 (by mol)) copolymer | 10 parts |
| Sodium polyacrylate | 10 parts |
| Polyacrylic acid | 10 parts |
| N-Methyl-N-vinylacetamide/potassium acrylate (60/40 (by weight)) copolymer | 1 part |
| Magnesium aluminometasilicate | 5 parts |
| Aluminum potassium sulfate | 5 parts |
| Sodium hydroxide | 0.5 parts |
| Ethanol | 30 parts |
| Water | 28 parts |
| Ascorbic acid-2-glucoside | 0.5 parts |

Formulation

An ethanol dispersion solution of ascorbic acid-2-glucoside, sodium polyacrylate ("Viscomate F480SS" produced by Showa Denko K.K.), sodium acrylate/acrylic acid (80/20 (by mol)) copolymer (partially neutralized polyacrylate) and polyacrylic acid, N-methyl-N-vinylacetamide copolymer and magnesium aluminometasilicate ("Neusilin" produced by Fuji Chemical Industry Co., Ltd.) was added all at once to an aqueous solution containing sodium hydroxide and aluminum potassium sulfate and kneaded. The obtained sol was shaped with a clearance of 0.5 mm, sealed, ripened at room temperature for 7 days and then taken out from the container to obtain a plastering agent. When the gel was touched with a finger, the gel was extended and exhibited strong resiliency. The pH of the gel was measured in the same manner as in Example 1 and found to be 8.5. Also, the obtained plastering agent was exposed to 25° C. and 60% at relative humidity for 24 hours and thereafter measured on the ball tack value at an inclined angle of 30° according to the Tack Test Method of JIS Z0237, as a result, the ball tack value was 15.

EXAMPLE 5

| Raw Material Blending Ratio | |
|---|---|
| Sodium acrylate/acrylic acid (70/30 (by mol)) copolymer | 1 part |
| Polyacrylic acid | 1 part |
| N-Vinylacetamide/sodium acrylate (9/1 (by weight)) copolymer | 3 parts |
| Purified water | 64.88 parts |
| Aluminum hydroxide-sodium bicarbonate co-precipitate | 0.05 parts |
| Aluminum lactate | 0.05 parts |
| 1,3-Butanediol | 30 parts |
| Aqueous 10% ammonia solution | 0.01 part |
| Magnesium ascorbic acid-2-phosphate | 0.01 part |

Formulation 1,3-butanediol dispersion solution of magnesium ascorbic acid-2-phosphate ("Ascorbic Acid PM" produced by Showa Denko K.K.), sodium acrylate/acrylic acid (70/30 (by mol)) copolymer (partially neutralized polyacrylate) ("Viscomate NP-600" produced by Showa Denko K.K.) polyacrylic acid, N-vinylacetamide/sodium acrylate (9/1 (by weight)) copolymer and aluminum hydroxide-sodium bicarbonate co-precipitate ("Kumulite" produced by Kyowa Chemical Industry Co., Ltd.) was kneaded while adding these to an aqueous solution containing ammonia and aluminum lactate. The obtained sol was coated on a polypropylene-made liner by a knife coater with a clearance of 0.5 mm, a nonwoven fabric was then affixed on the sol, the whole was placed in an aluminum laminate bag, and the bag was heat-sealed. After ripening for 3 days, a plastering agent was obtained. When the gel on the nonwoven fabric was touched with a finger, the gel was slightly extended and exhibited strong resiliency. The pH of the gel was measured in the same manner as in Example 1 and found to be 6.5. Also, the obtained plastering agent was exposed to 25° C. and 60% at relative humidity for 24 hours and thereafter measured on the ball tack value at an inclined angle of 30° according to the Tack Test Method of JIS 20237, as a result, the ball tack value was 10.

COMPARATIVE EXAMPLE 1

| Raw Material Blending Ratio | |
|---|---|
| Sodium polyacrylate | 4 parts |
| Glycerin | 30 parts |
| Purified water | 61 parts |
| magnesium hydroxide-aluminum hydroxide co-precipitate | 1 part |
| Diisopropanolamine | 1 part |
| Magnesium ascorbic acid-2-phosphate | 3 parts |

Formulation

A glycerin dispersion solution of magnesium ascorbic acid-2-phosphate ("Ascorbic Acid PM" produced by Showa Denko K.K.), sodium polyacrylate ("Viscomate F480SS" produced by Showa Denko K.K.) and magnesium hydroxide-aluminum hydroxide co-precipitate ("Sanalmin" produced by Kyowa Chemical Industry Co., Ltd.) was kneaded while gradually adding these to an aqueous solution of diisopropanolamine. The obtained sol was coated on a polypropylene-made liner by a knife coater with a clearance of 0.5 mm, a nonwoven fabric was then affixed on the sol, the whole was placed in an aluminum laminate bag, and the bag was heat-sealed. After ripening for 3 days, a plastering agent was obtained. When the gel on the nonwoven fabric was touched with a finger, the gel exhibited no resiliency and clung to the finger. Also, the nonwoven fabric was entirely wetted with the sol.

COMPARATIVE EXAMPLE 2

| Raw Material Blending Ratio | |
|---|---|
| Sodium acrylate/acrylic acid (70/30 (by mol)) copolymer | 4 parts |
| Purified water | 61.5 parts |
| Dihydroxyaluminum aminoacetate | 0.5 parts |
| Dried aluminum hydroxide gel | 0.5 parts |
| D-Sorbitol solution | 30 parts |
| Diisopropanolamine | 0.5 parts |
| Zinc ascorbic acid-2-phosphate | 3 parts |

Formulation

A D-sorbitol (70 w/v % aqueous solution of D-sorbitol) dispersion solution of Zinc ascorbic acid-2-phosphate, sodium acrylate/acrylic acid (70/30 (by mol)) copolymer (partially neutralized polyacrylate) and a dihydroxyaluminum aminoacetate ("GLYCINAL" produced by Kyowa Chemical Industry Co., Ltd.) and aluminum hydroxide ("Dried Aluminum Hydroxide Gel S-100" produced by Kyowa Chemical Industry Co., Ltd.) was kneaded while adding these to an aqueous solution of diisopropanolamine. The obtained sol was coated on a polypropylene-made liner by a knife coater with a clearance of 0.5 mm, a nonwoven fabric was then affixed on the sol, the whole was placed in an aluminum laminate bag, and the bag was heat-sealed. After ripening for 3 days, a plastering agent was obtained. When the gel on the plastering agent was touched with a finger, the gel exhibited no resiliency and clung to the finger. Also, the nonwoven fabric was entirely wetted with the sol.

INDUSTRIAL APPLICABILITY

As described in the foregoing pages, the hydrous gel of the present invention can stably hold an ascorbic acid or a derivative thereof, has high gel strength, exhibits good adhesion to an adherend, causes no liquid syneresis, and has a simple composition to facilitate the preparation. By using the hydrous gel of the present invention, a cosmetic material and the like capable of maximally bringing out the effect of an ascorbic acid or a derivative thereof on skin or the like can be provided.

The invention claimed is:

1. A process for producing a hydrous gel, comprising preparing a mixture containing at least two polymers comprising acrylic acid/sodium acrylate copolymer and at least one of polyacrylic acid and sodium polyacrylate crosslinked with an alumina magnesium hydroxide, and water, and at least one ascorbic acid compound selected from the group consisting of ascorbic acid, ascorbic acid-2-phosphoric ester, ascorbic acid-2-pyrophosphoric ester, ascorbic acid-2-triphosphoric ester, ascorbic acid-2-polyphosphoric ester, ascorbic acid-2,3-diphosphoric ester, ascorbic acid-2,6-diphosphoric ester, ascorbic acid-2-sulfuric ester, ascorbic acid-6-palmitic ester, ascorbic acid-2,6-palmitic ester, ascorbic acid-2-glucoside, ascorbic acid-2-O-glucoside-6-palmitic ester, ascorbic acid-5,6-benzylidene, ascorbic acid-5,6-propylidene and their metal salts, ammonium salts and alkyl- or hydroxyalkyl-substituted ammonium salts, and heating said mixture at 25 to 65° C.,
wherein the pH when said hydrous gel is 100-fold diluted with purified water is adjusted to 6.5 to 8.5.

2. The process for producing a hydrous gel as claimed in claim 1, wherein the pH is adjusted to 7.0 to 8.0.

3. The process for producing a hydrous gel as claimed in claim 1, wherein said heating is at 35 to 65° C.

4. The process for producing a hydrous gel as claimed in claim 2, wherein said heating is at 35 to 65° C.

5. The process for producing a hydrous gel as claimed in claim 1, wherein said heating is at 35 to 55° C.

6. The process for producing a hydrous gel as claimed in claim 2, wherein said heating is at 35 to 55° C.

7. The process for producing a hydrous gel as claimed in claim 1, wherein said heating is at 40 to 50° C.

8. The process for producing a hydrous gel as claimed in claim 2, wherein said heating is at 40 to 50° C.

9. The process for producing a hydrous gel as claimed in claim 1, wherein the acrylic acid/sodium acrylate copolymer is present in an amount of 1 part by mass per 100 parts by mass of the hydrous gel.

10. The process for producing a hydrous gel as claimed in claim 1, wherein the acrylic acid/sodium acrylate copolymer is present in an amount of 10 parts by mass per 100 parts by mass of the hydrous gel.

* * * * *